(12) United States Patent
Shetty

(10) Patent No.: US 10,675,322 B2
(45) Date of Patent: Jun. 9, 2020

(54) HERBAL FORMULATION FOR MANAGEMENT OF METABOLIC DISORDERS AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 141 days.

(21) Appl. No.: 16/030,408

(22) Filed: Jul. 9, 2018

(65) Prior Publication Data

US 2018/0318374 A1 Nov. 8, 2018

Related U.S. Application Data

(60) Provisional application No. 62/531,223, filed on Jul. 11, 2017.

(51) Int. Cl.
*A61K 36/00* (2006.01)
*A61K 36/53* (2006.01)
(Continued)

(52) U.S. Cl.
CPC .......... *A61K 36/53* (2013.01); *A61K 9/2068* (2013.01); *A61K 33/00* (2013.01); *A61K 33/06* (2013.01); *A61K 33/24* (2013.01); *A61K 33/242* (2019.01); *A61K 33/26* (2013.01); *A61K 33/30* (2013.01); *A61K 33/34* (2013.01); *A61K 35/02* (2013.01); *A61K 35/04* (2013.01); *A61K 35/614* (2013.01); *A61K 35/618* (2013.01); *A61K 36/185* (2013.01); *A61K 36/24* (2013.01); *A61K 36/264* (2013.01); *A61K 36/28* (2013.01); *A61K 36/324* (2013.01); *A61K 36/328* (2013.01); *A61K 36/35* (2013.01); *A61K 36/428* (2013.01); *A61K 36/48* (2013.01); *A61K 36/484* (2013.01); *A61K 36/58* (2013.01); *A61K 36/59* (2013.01);
(Continued)

(58) Field of Classification Search
CPC .................. A61K 36/00; A61K 33/00
See application file for complete search history.

(56) References Cited

PUBLICATIONS

Yadav et al., "A novel herbomineral formulation Sahaj Vati as shelf life enhancer of nutraceuticals based on aflatoxin inhibitory and antioxidant activity," Indian J Pharm Sci 79(1):29-34, Jan.-Feb. 2017.*

(Continued)

*Primary Examiner* — Rosanne Kosson
(74) *Attorney, Agent, or Firm* — Pilloff Passino & Cosenza LLP; Sean A. Passino; Rachel K. Pilloff

(57) ABSTRACT

Herbal formulation for treatment/management of metabolic disorders and related complications are disclosed herein. The disclosed herbal formulation includes herb and mineral elements which facilitate in treating lipid metabolism disorders including Dyslipidemia, obesity, etc. The formulation disclosed herein may also be used in treating any condition associated with Dyslipidemia such as cardio vascular diseases, cerebro vascular diseases, stroke, pancreatitis, steatohepatitis, atherosclerosis, hyperglycemia, metabolic syndrome, etc. Further, the disclosed formulation may also be instrumental as anti-atherosclerotic and hypolipidemic agent.

21 Claims, 11 Drawing Sheets

(51) Int. Cl.

| | | |
|---|---|---|
| *A61K 36/328* | (2006.01) | |
| *A61K 35/04* | (2006.01) | |
| *A61K 33/00* | (2006.01) | |
| *A61K 33/34* | (2006.01) | |
| *A61K 35/614* | (2015.01) | |
| *A61K 35/618* | (2015.01) | |
| *A61K 33/26* | (2006.01) | |
| *A61K 33/24* | (2019.01) | |
| *A61K 33/30* | (2006.01) | |
| *A61K 47/44* | (2017.01) | |
| *A61P 3/06* | (2006.01) | |
| *A61P 3/04* | (2006.01) | |
| *A61K 9/20* | (2006.01) | |
| *A61K 36/9068* | (2006.01) | |
| *A61K 36/67* | (2006.01) | |
| *A61K 35/02* | (2015.01) | |
| *A61K 36/9066* | (2006.01) | |
| *A61K 36/81* | (2006.01) | |
| *A61K 36/28* | (2006.01) | |
| *A61K 36/35* | (2006.01) | |
| *A61K 36/68* | (2006.01) | |
| *A61K 36/58* | (2006.01) | |
| *A61K 36/264* | (2006.01) | |
| *A61K 36/8905* | (2006.01) | |
| *A61K 36/24* | (2006.01) | |
| *A61K 36/428* | (2006.01) | |
| *A61K 36/484* | (2006.01) | |
| *A61K 36/48* | (2006.01) | |
| *A61K 36/61* | (2006.01) | |
| *A61K 36/59* | (2006.01) | |
| *A61K 36/185* | (2006.01) | |
| *A61K 36/85* | (2006.01) | |
| *A61K 36/324* | (2006.01) | |
| *A61K 33/242* | (2019.01) | |
| *A61K 33/06* | (2006.01) | |

(52) U.S. Cl.
CPC .............. *A61K 36/61* (2013.01); *A61K 36/67* (2013.01); *A61K 36/68* (2013.01); *A61K 36/81* (2013.01); *A61K 36/85* (2013.01); *A61K 36/8905* (2013.01); *A61K 36/9066* (2013.01); *A61K 36/9068* (2013.01); *A61K 47/44* (2013.01); *A61P 3/04* (2018.01); *A61P 3/06* (2018.01); *A61K 2236/15* (2013.01); *A61K 2236/331* (2013.01)

(56) References Cited

PUBLICATIONS

The Government of India, Biological Diversity Act, 2002.†

\* cited by examiner
† cited by third party

HERBAL FORMULATION FOR MANAGEMENT OF METABOLIC DISORDERS AND METHOD OF PREPARATION THEREOF

CROSS REFERENCE TO RELATED APPLICATION

This application is based on and derives the benefit of U.S. Provisional Application 62/531,223 filed on Jul. 11, 2017, the contents of which are incorporated herein by reference.

TECHNICAL FIELD

The embodiments disclosed in this specification relates to herbal formulation effective in the treatment, management and prevention of metabolic disorders, and more particularly in the treatment of dyslipidemia. It also relates to the process of preparation of such formulation.

BACKGROUND

Metabolic disorders occur due to disruption of a metabolic process in human body. The synthesis and breakdown of biomolecules such as fats, proteins and carbohydrates in our body occur through highly regulated set of metabolic pathways. These metabolic processes if interrupted at any level could lead to the abnormal accumulation/lack of certain biomolecules which could lead to a metabolic disorder. Depending on the type of biomolecules the metabolic disorders maybe classified as lipid metabolism disorders, Iron metabolism disorders, Phosphorous metabolism disorders, Calcium metabolism disorders, etc.

Dyslipidemia is a condition that occurs due to abnormality in lipid metabolism. It is a variation in lipid levels in blood plasma. This variation in lipids levels may be due to increased or decreased amount of Cholesterol and/or Triglyceride (TG) in plasma. Commonly known form of dyslipidemia is hyperlipidemia which is a condition due to elevated level of lipids in blood.

Primarily, dyslipidemia may be caused as a result of genetic mutation. In such case, children may also be affected. However, secondary causes wherein adults are the most affected include sedentary lifestyle, alcohol overuse, Diabetes, Chronic kidney diseases, liver diseases and so on. In recent times, lifestyle with excessive consumption of trans-fats and saturated fats, and with physical inactivity is soon becoming a common cause for dyslipidemia related obesity. In case of diabetic patients, prolonged increased levels of insulin may also lead to dyslipidemia.

Dyslipidemia itself is not a life-threatening condition. However, it leads to conditions such as hypercholesterolemia, hypertriglyceridemia, steatohepatitis, atherosclerosis, obesity, hyperglycemia, metabolic syndrome, etc. Conditions such as obesity, atherosclerosis, hyperglycemia etc further increase the risks of grave complications such as coronary artery diseases, stroke, pancreatitis, peripheral arterial diseases, etc. In Diabetic patients, especially, the risks of such conditions are higher.

There exist many methods of treatment for Dyslipidemia and related disorders. Method of treatment includes changes in dietary habits and lifestyle, allopathic medication, procedural approaches, etc. Statins, fibrates and niacin/nicotinic acid are classes of lipid lowering drugs that are generally used. Other commonly known classes of drugs include bile acid binding resins, cholesterol absorption inhibitors, monoclonal antibodies, etc. However, these drugs may have undesirable side effects.

Alternatively, ayurvedic interventions are also known in treating Dyslipidemia and related disorders. Many herbal formulations have been developed based on the knowledge of the healing properties of various herbs. Formulations having herbs such as *Commiphora mukul, Boswellia serrata, Semecarpus anacardium Strychnox nux vomica, Terminalia arjuna, Rubia cordifolia, Bacopa monnieri, Cyprerus rotundus, Emblica officinalis, Emblica ribes, Piper longum, Piper nigrum, Plumbago zeylanica, Terminala bellarica, Terminala chebula* and *Zinger oficinale*, etc. have been developed. However, the effectiveness of such formulations is arguable. There exists a need for an effective method of treating/managing Dyslipidemia and related disorders.

Objects of the Disclosed Embodiments

The principal object of the embodiments disclosed herein is to provide a composition and method of treating Metabolic disorders.

A second object of the embodiments disclosed herein is to provide a composition and method of preventing Metabolic disorders.

Another object of the embodiments disclosed herein is to provide a composition and method of treating Dyslipidemia.

Another object of the embodiments disclosed herein is to provide a composition and method of preventing Dyslipidemia.

Another object of the embodiments disclosed herein is to provide a composition and method of treating Obesity.

Another object of the embodiments disclosed herein is to provide a composition and method of managing Obesity.

Another object of the embodiments disclosed herein is to provide a herbal formulation and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which:

FIG. 1(*b*) depicts a flowchart for the preparation of Abhraka Bhasma;

FIG. 1(*c*) depicts a flowchart for the preparation of Mukta shukti Bhasma;

FIG. 1(*d*) depicts a flowchart for the preparation of Loha Bhasma;

FIG. 1(*e*) depicts a flowchart for the preparation of Trivanga Bhasma;

DETAILED DESCRIPTION

Figure 1A:
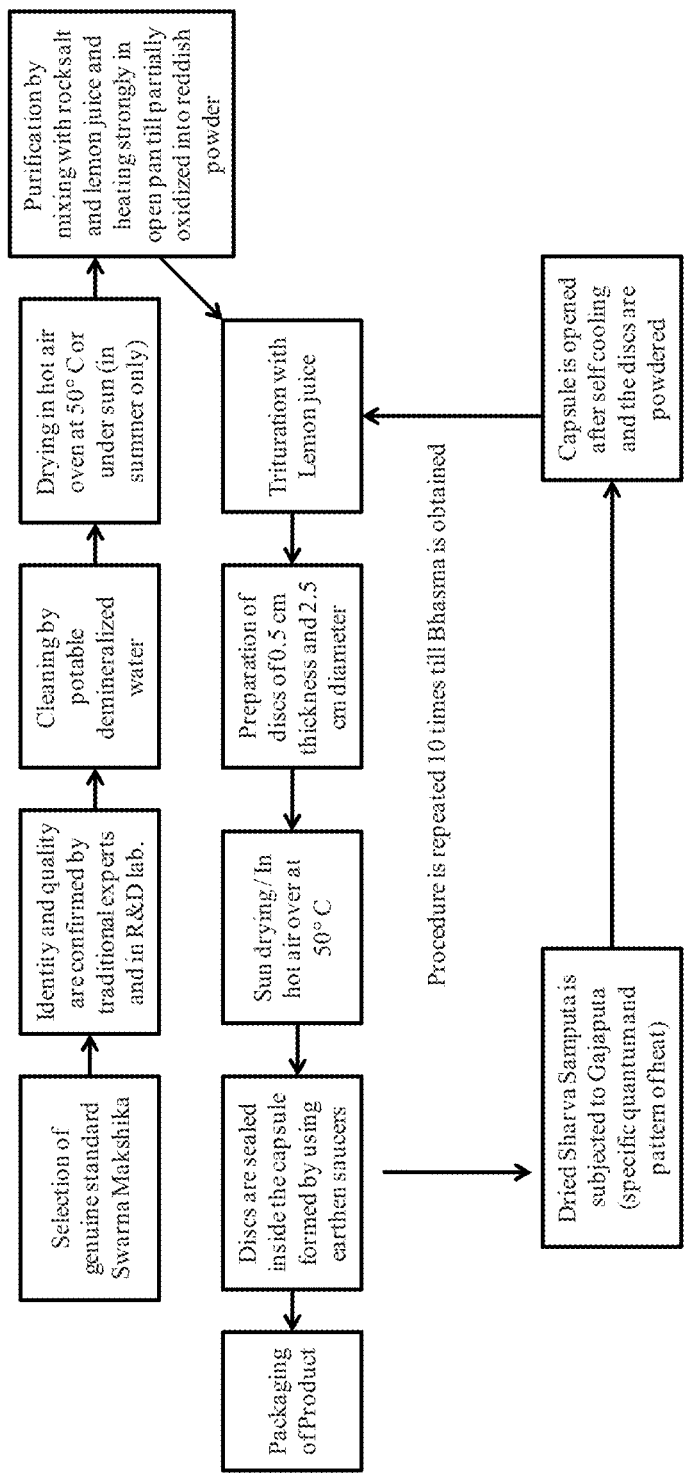
FIG. 1(*a*) depicts a flowchart for the preparation of Swarna Makshika Bhasma.
FIG. 1(f) depicts a flowchart for the preparation of Pravala Bhasma.
Figure 1B:
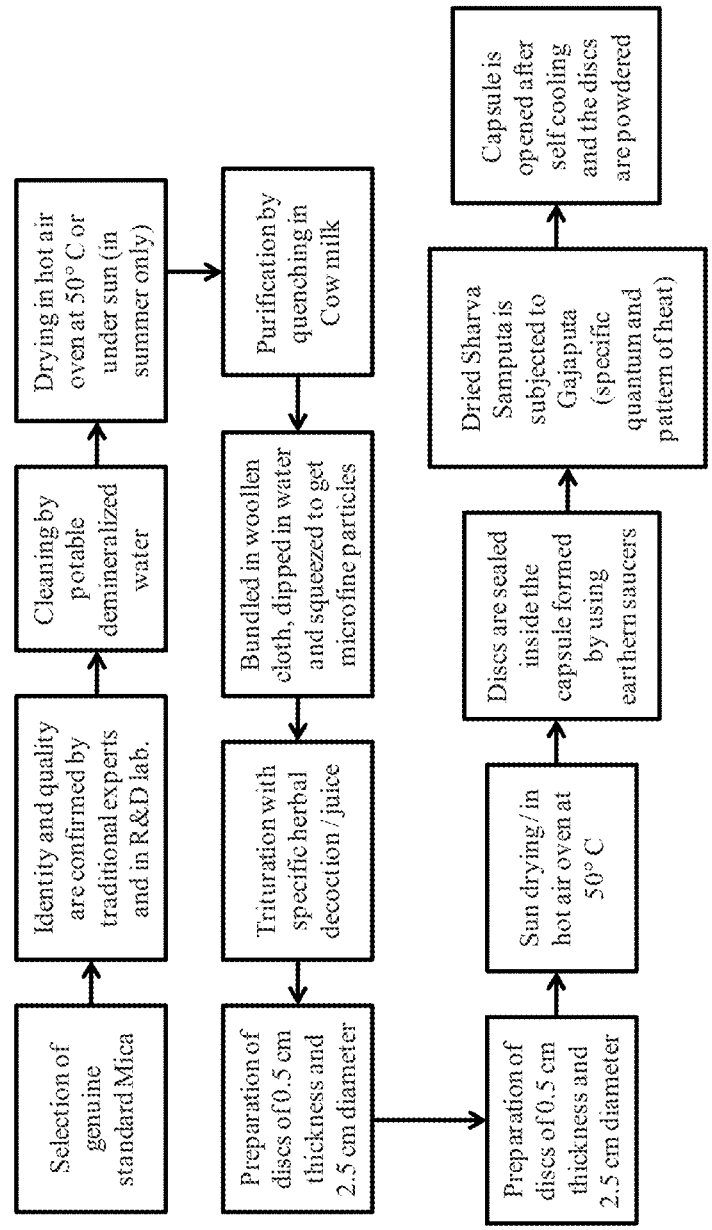
Figure 1C:
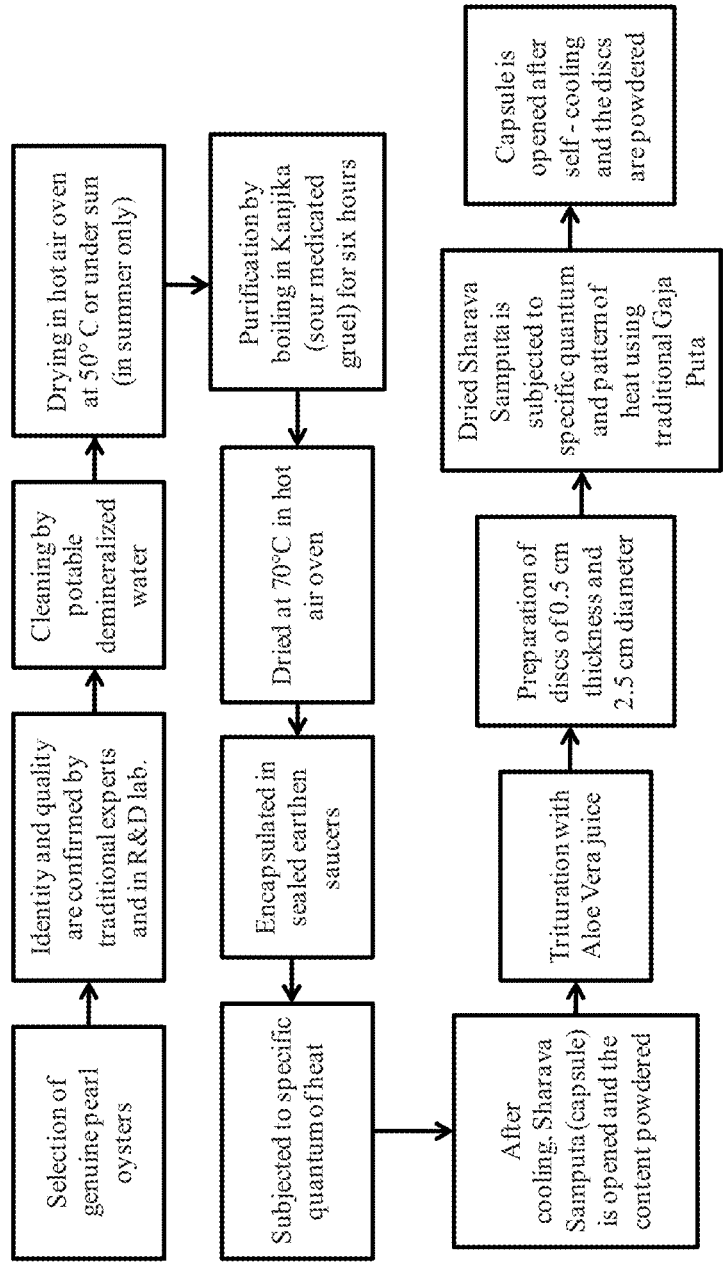
Figure 1D:
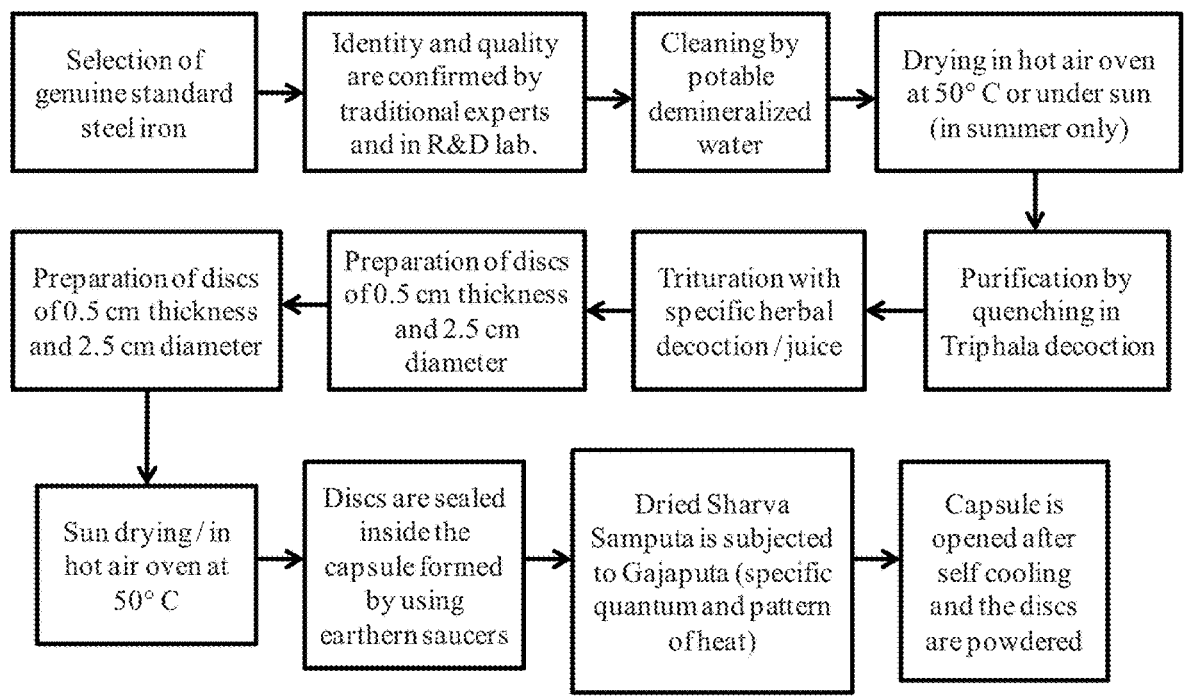
Figure 1E:
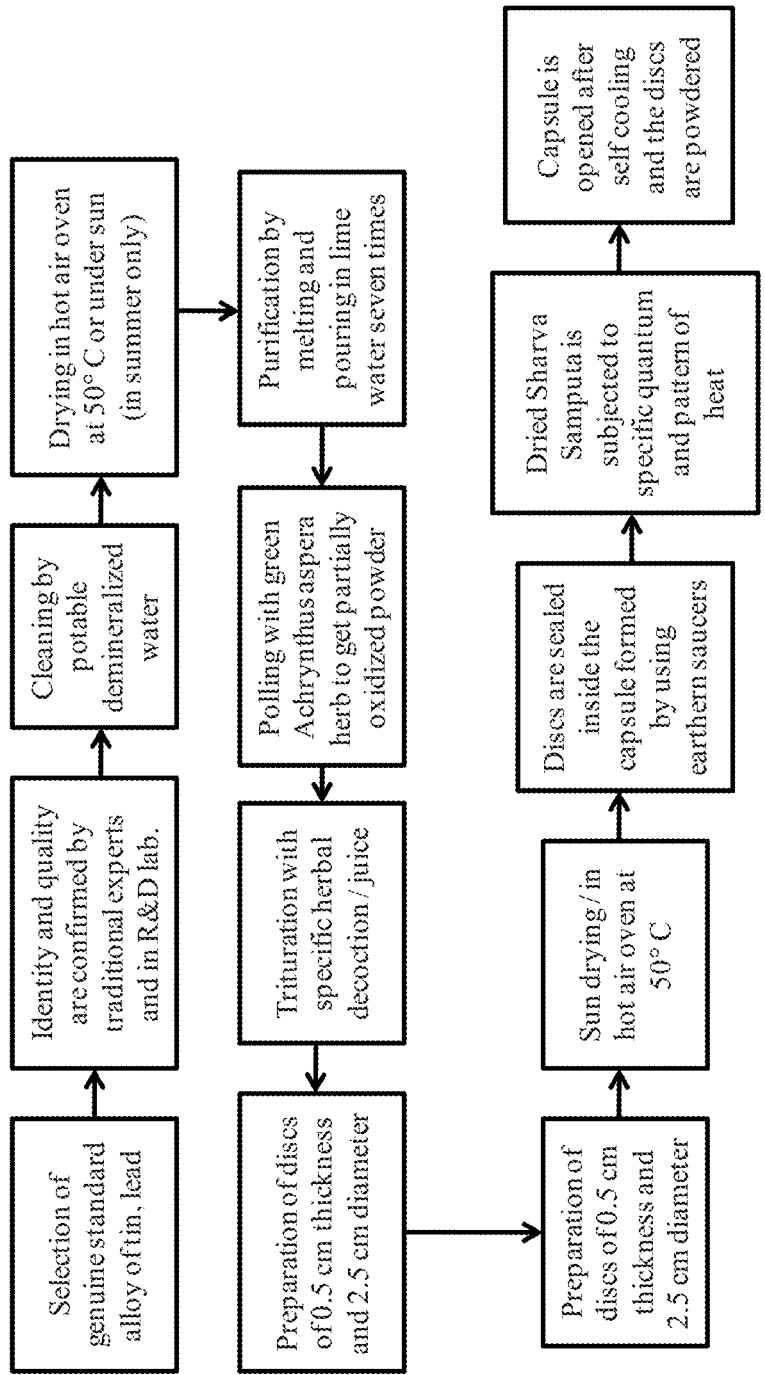
Figure 1F:
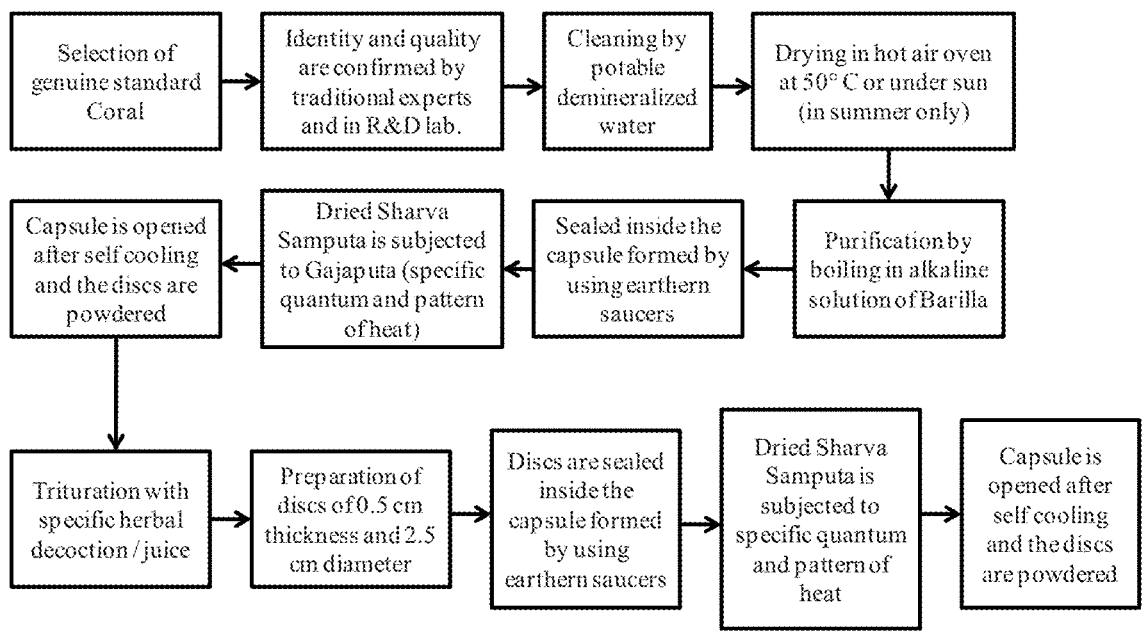

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a herbal formulation of therapeutic value, and process for the preparation of the formulation. The herbal formulation disclosed herein is useful in the treatment/management/prevention of metabolic disorders. Metabolic disorders in various embodiments herein include lipid metabolism disorders. Further, it is instrumental in the treatment/management/prevention of Dyslipidemia and related disorders. In various embodiments herein, Dyslipidemia may include any condition associated with abnormal lipid levels such as hyperlipidemia, hypolipidemia, hypercholesterolemia, hypertriglyceridemia, etc. Further dyslipidemia related disorders may include any condition associated with abnormal lipid levels such as cardio vascular diseases, cerebrovascular diseases, stroke, pancreatitis, steatohepatitis, atherosclerosis, obesity, hyperglycemia, metabolic syndrome, etc. Furthermore, the disclosed formulation may also be useful in treating and managing Obesity. The herbal formulation disclosed herein may also be instrumental as an anti-atherosclerotic and hypolipidemic agent. Accordingly, the embodiments disclosed herein achieve a method for the treatment of metabolic disorders including conditions such as dyslipidemia and obesity.

Formulation

The disclosed embodiments herein provide herbal formulation having herbs and minerals. In an embodiment, the herbal formulation includes a herb element and a mineral element. In another embodiment, the herbal formulation includes a herb element, a mineral element and a suitable excipient.

Herb Element

In an embodiment, the herb element includes the herbs *Premna integrifolia*, *Plumbago rosea* and *Commiphora mukul* or their extracts, or the active ingredients extracted from these herbs. In another embodiment, the herb element further includes at least one of the herbs selected from *Emblica officinalis*, *Terminalia bellerica*, *Terminalia chubula*, *Zingiber officinalis*, *Piper longum*, *Piper nigrum*, *Embelia ribes*, *Curcuma longa*, *Terminalia arjuna*, *Sida rhombifolia*, *Withania somnifera*, *Inula racemose*, *Punica grnatum*, *Nardostachys jatamansi*, *Boerhavia diffusa*, *Picrorhiza kurroa*, *Ocimum sanctum*, *Azadirachta indica*, *Aristolochia indica*, *Aegle marmelos*, *Cyperus rotundas*, *Hemidesmus indicus*, *Trichosanthus dioica*, *Sanatalum album*, *Glycerrhiza glabra*, *Woodfordia fruiticosa*, *Mucuna pruriens*, *Myrica nagi*, *Syzygium cumini*, *Tinospora cordifolia* and *Bamboo manna* or their extracts, or the active ingredients extracted from these herbs.

In an embodiment, the herb element may include specific parts of the herb (herb component) such as roots, fruits, stem, leaves, rhizome, etc. In an embodiment, the herb element includes roots of *Premna integrifolia*, *Plumbago rosea*, *Sida rhombifolia* *Withania somnifera*, *Inula racemose*, *Boerhavia diffusa*, *Picrorhiza kurroa*, *Aristolochia indica*, *Aegle marmelos*, *Cyperus rotundas*, *Hemidesmus indicus* and *Glycerrhiza glabra*; fruits of *Emblica officinalis*, *Terminalia bellerica*, *Terminalia chubula*, *Piper longum*, *Piper nigrum* and *Embelia ribes*; rhizome of *Zingiber officinalis*, *Curcuma longa* and *Nardostachys jatamansi*; stem bark of *Terminalia arjuna*, *Azadirachta indica*, *Myrica nagi* and *Syzygium cumini*; exocarp and epicarp of *Punica grnatum*; leaves of *Ocimum sanctum*; whole plant of *Trichosanthus dioica*; heartwood of *Sanatalum album*; flowers of *Woodfordia fruiticosa*; seeds of *Mucuna pruriens*; and stem of *Tinospora cordifolia*. However, it is also within the scope of the claims provided herein for the herbal formulation to include other herb components such as leaf, flowers, etc. without otherwise deterring intended function of the herbal formulation.

The herb element may also include any form of secretion, resin or discharge that may be exuded by the herb or any part of the herb. In an embodiment, the herb element may include secretion of *Bamboo manna* and oleo-gum resin of *Commophora mukul*. However, it is also within the scope of the claims provided herein for the herbal formulation to include other herb components such as leaf, flowers, etc. without otherwise deterring intended function of the herbal formulation.

The herb component of the herbs, disclosed herein, maybe included in the formulation in any form that is generally known in the field. For example, the herb component may be processed to form extracts, dried, powdered, pelleted, concentrated, etc. In an embodiment, the herb components are dried and powdered which is further incorporated into the formulation. In another embodiment, the herb component includes stem (for example: stem of *Tinospora cordifolia*) which may be processed by methods known in the field to yield a starchy extract which is further used in the formulation.

In an embodiment, the herb element includes the herbs *Premna integrifolia*, *Plumbago rosea* and *Commiphora mukul* (Guggulu) in an amount in the range of 2 to 6 wt %. Further, in another embodiment, the herb element includes at least one of *Emblica officinalis*, *Terminalia bellerica*, *Terminalia chubula*, *Zingiber officinalis*, *Piper longum*, *Piper nigrum*, *Embelia ribes*, *Curcuma longa*, *Terminalia arjuna*, *Sida rhombifolia*, *Withania somnifera*, *Inula racemose*, *Punica grnatum*, *Nardostachys jatamansi*, *Boerhavia diffusa*, *Picrorhiza kurroa*, *Ocimum sanctum*, *Azadirachta indica*, *Aristolochia indica*, *Aegle marmelos*, *Cyperus rotundas*, *Hemidesmus indicus*, *Trichosanthus*

*dioica, Sanatalum album, Glycerrhiza glabra, Woodfordia fruiticosa, Mucuna pruriens, Myrica nagi, Syzygium cumini, Tinospora cordifolia* and *Bamboo manna* in an amount in the range of 1 to 4 wt %.

Mineral Element

In an embodiment, the mineral element includes Bhasmas or calcined preparations such as Abhraka bhasma, Swarnamakshika bhasma, Pravala bhasma, Muktashukti Bhasma, Loha bhasma, and Trivanga bhasma. Alternatively, the mineral element may also be selected from a group consisting of at least one of Mica, coral, iron, copper pyrite, etc. In the disclosed embodiments, the bhasmas along with the herb element form bioavailable herbo-mineral complexes which are useful in treating, preventing and managing metabolic disorders. In an embodiment, the mineral element further includes Shilajit. However, it is also within the scope of claims provided herewith for the herbal formulation to include, as a substitute or additionally, other similar calcined preparations or minerals without otherwise deterring from the intended function of the herbal formulation.

In an embodiment, the mineral element includes shilajit in an amount in the range of 2 to 6 wt %. In another embodiment, the mineral element includes at least one of Abhraka bhasma, Swarnamakshika bhasma, Pravala bhasma, Muktashukti Bhasma, Loha bhasma and Trivanga bhasma in an amount in the range of 1 to 4 wt %.

The disclosed formulation, in the various embodiments herein, may further include a suitable excipient. The suitable excipients include solvents, binders, lubricants, herbal carriers, oils and salts that are generally known in the art. In a preferred embodiment, the excipient includes *acacia* gum.

Further, the amount of herb element and mineral element that may be included in the various embodiments of the disclosed formulation may be in the range of 0 to 6 wt %. In an embodiment, the formulation includes *Premna integrifolia* (2 to 6 wt %), *Plumbago rosea* (2 to 6 wt %), *Commiphora mukul* (2 to 6 wt %), Shilajit (2 to 6 wt %), Abhraka bhasma (1 to 4 wt %), Swarnamakshika bhasma (1 to 4 wt %), Pravala bhasma (1 to 4 wt %), Muktashukti Bhasma (1 to 4 wt %), Loha bhasma (1 to 4 wt %) and Trivanga bhasma (1 to 4 wt %).

In another embodiment, the formulation includes *Premna integrifolia* (2 to 6 wt %), *Plumbago rosea* (2 to 6 wt %), *Commiphora mukul* (2 to 6 wt %), *Emblica officinalis* (1 to 4 wt %), *Terminalia bellerica* (1 to 4 wt %), *Terminalia chubula* (1 to 4 wt %), *Zingiber officinalis* (1 to 4 wt %), *Piper longum* (1 to 4 wt %), *Piper nigrum* (1 to 4 wt %), *Embelia ribes* (1 to 4 wt %), *Curcuma longa* (1 to 4 wt %), *Terminalia arjuna* (1 to 4 wt %), *Sida rhombifolia* (1 to 4 wt %), *Withania somnifera* (1 to 4 wt %), *Inula racemose* (1 to 4 wt %), *Punica grnatum* (1 to 4 wt %), *Nardostachys jatamansi* (1 to 4 wt %), *Boerhavia diffusa* (1 to 4 wt %), *Picrorhiza kurroa* (1 to 4 wt %), *Ocimum sanctum* (1 to 4 wt %), *Azadirachta indica* (1 to 4 wt %), *Aristolochia indica* (1 to 4 wt %), *Aegle marmelos* (1 to 4 wt %), *Cyperus rotundas* (1 to 4 wt %), *Hemidesmus indicus* (1 to 4 wt %), *Trichosanthus dioica* (1 to 4 wt %), *Sanatalum album* (1 to 4 wt %), *Glycerrhiza glabra* (1 to 4 wt %), *Woodfordia fruiticosa* (1 to 4 wt %), *Mucuna pruriens* (1 to 4 wt %), *Myrica nagi* (1 to 4 wt %), *Syzygium cumini* (1 to 4 wt %), *Tinospora cordifolia* (1 to 4 wt %), *Bamboo manna* (1 to 4 wt %), Shilajit (2 to 6 wt %), Abhraka bhasma (1 to 4 wt %), Swarnamakshika bhasma (1 to 4 wt %), Pravala bhasma (1 to 4 wt %), Muktashukti Bhasma (1 to 4 wt %), Loha bhasma (1 to 4 wt %) and Trivanga bhasma (1 to 4 wt %).

The amount of gum *acacia* included in the various embodiments herein may be any amount suitable to perform the activity of an excipient. In an embodiment, the formulation may include gum *acacia* in the range of 0 to 50 mg per 500 mg of the formulation, preferably 10 wt %.

However, it is apparent that slight variations in the amount of the ingredients may be performed without otherwise deterring from the intended function of the herbal formulation.

The herbal formulation disclosed herein may be formulated in various dosage forms such that it is suitable for oral administration. The herbal formulation may be in the form of tablets, pellets, lozenges, granules, capsules, solutions, emulsions, suspensions, or any other form suitable for use. In an embodiment, the herbal formulation is formulated in the form of tablets, preferably 500 mg tablets. For example: Table 1A depicts the quantities of each ingredient in a 500 mg tablet.

Further disclosed herein, is a tablet for treating/preventing/managing metabolic disorders. In an embodiment, the tablet is a 500 mg tablet having herb element, mineral element and an excipient as depicted in Table 1A.

TABLE 1A

Each 500 mg tablet includes:

| S. NO | SANSKRIT NAME | PART USED | BOTANICAL NAME | QUANTITY |
|---|---|---|---|---|
| 1 | Agnimantha | Dried root | *Premna integrifolia* | 20 mg |
| 2 | Shuddha Chitraka | Purified dried root | *Plumbago rosea* | 20 mg |
| 3 | Amalaki | dried fruits | *Emblica officinalis* | 10 mg |
| 4 | Vibhitaki | dried fruits | *Terminalia bellerica* | 10 mg |
| 5 | Haritaki | dried fruit | *Terminalia chubula* | 10 mg |
| 6 | Shunthi | dry rhizome | *Zingiber officinalis* | 10 mg |
| 7 | Pippali | dry fruit | *Piper longum* | 10 mg |
| 8 | Maricha | dry fruit | *Piper nigrum* | 10 mg |
| 9 | Shilajith | Fossil resin | Asphaltum punjabicanum | 20 mg |
| 10 | Guggulu | oleo-gum-resin | *Commiphora mukul* | 20 mg |
| 11 | Vidanga | Dried fruit | *Embelia ribes* | 10 mg |
| 12 | Haridra | dried rhizomes | *Curcuma longa* | 10 mg |
| 13 | Arjuna | Dried stem bark | *Terminalia arjuna* | 10 mg |
| 14 | Bala | Dried root | *Sida rhombifolia* | 10 mg |
| 15 | Ashwagandha | Dried root | *Withania somnifera* | 10 mg |
| 16 | Pushkaramoola | Dried root | *Inula racemose* | 10 mg |
| 17 | Dadima | Dried exo and epicarp | *Punica grnatum* | 10 mg |
| 18 | Jatamamsi | Dried Rhizome | *Nardostachys jatamansi* | 10 mg |
| 19 | Punarnava | Dried root | *Boerhavia diffusa* | 10 mg |
| 20 | Katuki | Dried root | *Picrorhiza kurroa* | 10 mg |

TABLE 1A-continued

Each 500 mg tablet includes:

| S. NO | SANSKRIT NAME | PART USED | BOTANICAL NAME | QUANTITY |
|---|---|---|---|---|
| 21 | Tulasi | Dried leaves | *Ocimum sanctum* | 10 mg |
| 22 | Nimba | dried bark | *Azadirachta indica* | 10 mg |
| 23 | Ishwari | Dried root | *Aristolochia indica* | 10 mg |
| 24 | Bilwa | Dried root | *Aegle marmelos* | 10 mg |
| 25 | Mustaka | Dried root | *Cyperus rotundas* | 10 mg |
| 26 | Sariva | Dried root | *Hemidesmus indicus* | 10 mg |
| 27 | Patola | Dried whole plant | *Trichosanthus dioica* | 10 mg |
| 28 | Shvetachandana | Dried heartwood | *Sanatalum album* | 10 mg |
| 29 | Yashtimadhu | Dried root | *Glycerrhiza glabra* | 10 mg |
| 30 | Dhataki | Dried flowers | *Woodfordia fruiticosa* | 10 mg |
| 31 | Kapikacchu | Dried seeds | *Mucuna pruriens* | 10 mg |
| 32 | Katphala | Dried stem bark | *Myrica nagi* | 10 mg |
| 33 | Jambu | Dried stem bark | *Syzygium cumini* | 10 mg |
| 34 | Guduchi Satva | Starchy extract of stem | *Tinospora cordifolia* | 10 mg |
| 35 | Abhraka bhasma | Mineral | Incinerated Mica | 10 mg |
| 36 | Swarnamaksika bhasma | Mineral | Incinerated Copper pyrite | 10 mg |
| 37 | Pravala bhasma | Mineral | Incinerated Coral | 10 mg |
| 38 | Muktashukti Bhasma | Mineral | | 10 mg |
| 39 | Loha bhasma | Mineral | Incinerated Iron | 10 mg |
| 40 | Trivanga bhasma | Mineral | Incinerated tin, lead and zinc | 10 mg |
| 41 | Vamshalochana | Secretion | Bamboo manna | 10 mg |
| 42 | Excipient | Gum | Gum acacia | 50 mg |

Embodiments of the disclosed formulation in tablet form were analyzed for parameters including physicochemical properties such as Tablet hardness, Loss on drying, Assay, Disintegration time, Ash value, etc and the results were noted. Table 2 depicts the results of the analysis performed to determine the physicochemical properties of an embodiment of the disclosed formulation. In an embodiment, the disclosed formulation tablets have the characteristics as depicted in Table 2. It will be apparent to those skilled in the art that many modifications, both to materials and methods, may be practiced without departing from the scope of the claims provided herewith.

TABLE 2

| TEST PARAMETERS | SPECIFICATIONS |
|---|---|
| Description | Blackish brown biconvex shaped tablets |
| Identification | Tests positive for piperine, guggulusteron. |
| Average weight | 500 mg ± 12.5 mg |
| Uniformity of weight | ±2.5% of actual average weight |
| Average tablet hardness | 2.0 kg/cm² |
| Loss on drying | 3.7% w/w |
| Methanol soluble extractive | 28.9% w/v |
| Chloroform soluble extractive | 7.9% w/v |
| Ash value | 18.0% w/w |
| Average Disintegration time | 28 minutes |

Method

Disclosed herein are embodiments of a method of preparing the herbal formulation. In an embodiment, the method includes,
    levigating bhasmas, Guggulu and shilajit in a grinder;
    adding herbs into the grinder; and
    adding grinding decoction while continuing grinding to obtain a ground mass.

The bhasmas include at least one of Abhraka bhasma, Swarnamakshika bhasma, Pravala bhasma, Muktashukti Bhasma, Loha bhasma, and Trivanga bhasma. The mixture of bhasmas, Guggulu and Shilajit may be in semi-solid form. In an embodiment, the levigation may be performed for a duration of around 3 hours.

Further, the herbs include finely powdered dried roots of *Premna integrifolia, Plumbago rosea, Sida rhombifolia, Withania somnifera, Inula racemose, Boerhavia diffusa, Picrorhiza kurroa, Aristolochia indica, Aegle marmelos, Cyperus rotundas, Hemidesmus indicus* and *Glycerrhiza glabra*; finely powdered dried fruits of *Emblica officinalis, Terminalia bellerica, Terminalia chubula, Piper longum, Piper nigrum* and *Embelia ribes*; finely powdered dried rhizome of *Zingiber officinalis, Curcuma longa* and *Nardostachys jatamansi*; finely powdered dried stem bark of *Terminalia arjuna, Azadirachta indica, Myrica nagi* and *Syzygium cumini*; finely powdered dried exocarp and epicarp of *Punica grnatum*; finely powdered dried leaves of *Ocimum sanctum*; finely powdered dried whole plant of *Trichosanthus dioica*; finely powdered dried heartwood of *Sanatalum album*; finely powdered dried flowers of *Woodfordia fruiticosa*; finely powdered dried seeds of *Mucuna pruriens*; secretions of *Bamboo manna* and starchy extract of stem of *Tinospora cordifolia*. In an embodiment, finely powdered herbs/herb components may be obtained by powdering and sieving the herb components through 80 mesh screen.

The grinding decoction is a decoction of herbs that may facilitate grinding. In an embodiment, the grinding decoction includes a decoction of at least one herb selected from a list consisting of: *Plantago ovata, Desmodium gangeticum, Uraria picta, Solanum indicum, Solanum xanthocarpum, Tribulus terrestris, Hordeum vulgare, Dolichos biforus, Asafoetida, Garcinia indica, Madhuca indica, Terminalia arjuna, Asparagus racemosus, Cuminum cyminum, Plumbagorosea, Baliospermum montanum, Aloe vera, Cedrus deodara, Acacia catechu, Andrographis paniculata, Pterocarpus marsupium, Adhatoda vasica, Carum carvi, Momordica charantia, Trigonella foenum graecum,* and *Areca catechu.*

The decoction may be obtained by any method of decocting generally known in the field. In an embodiment, the method of preparation of grinding decoction further includes, soaking the grinding herbs (i.e. powdered dry seeds of *Plantago ovata*, powdered dry plant of *Desmodium gangeticum*, powdered dry plant of *Uraria picta*, powdered dry roots of *Solanum indicum*, powdered dry plant of *Solanum xanthocarpum*, powdered dry fruits of *Tribulus terrestris*, Yavakshara alkali of *Hordeum vulgare*, powdered dry seeds of *Dolichos biflorus*, resin of *Asafoetida*, powdered dry fruit rind of *Garcinia indica*, powdered dry flower of *Madhuca indica*, powdered dry bark of *Terminalia arjuna*, fresh root of *Asparagus racemosus*, powdered dry fruit of *Cuminum cyminum*, powdered dry root of *Plumbagorosea*, powdered dry root of *Baliospermum montanum*, fresh leaf of *Aloe vera*, powdered dry heartwood of *Cedrus deodara*, powdered dry heartwood of *Acacia catechu*, fresh whole plant of *Andrographis paniculata*, powdered dry heartwood of *Pterocarpus marsupium*, fresh leaves of *Adhatoda vasica*, powdered dry cremocarps of *Carum carvi*, fresh fruit of *Momordica charantia*, powdered dry seeds of *Trigonella foenum graecum* and powdered dry nut of *Areca catechu*); and concentrating by boiling.

In another embodiment, soaking may be performed by soaking the grinding herbs in 16 parts of water overnight. In a further embodiment, concentrating may be performed by boiling at high temperature, preferably at about 80 to 85 degree Celsius, until ⅛th of the liquid remains. Concentration may be confirmed with the help of Brix meter.

Figure 2:
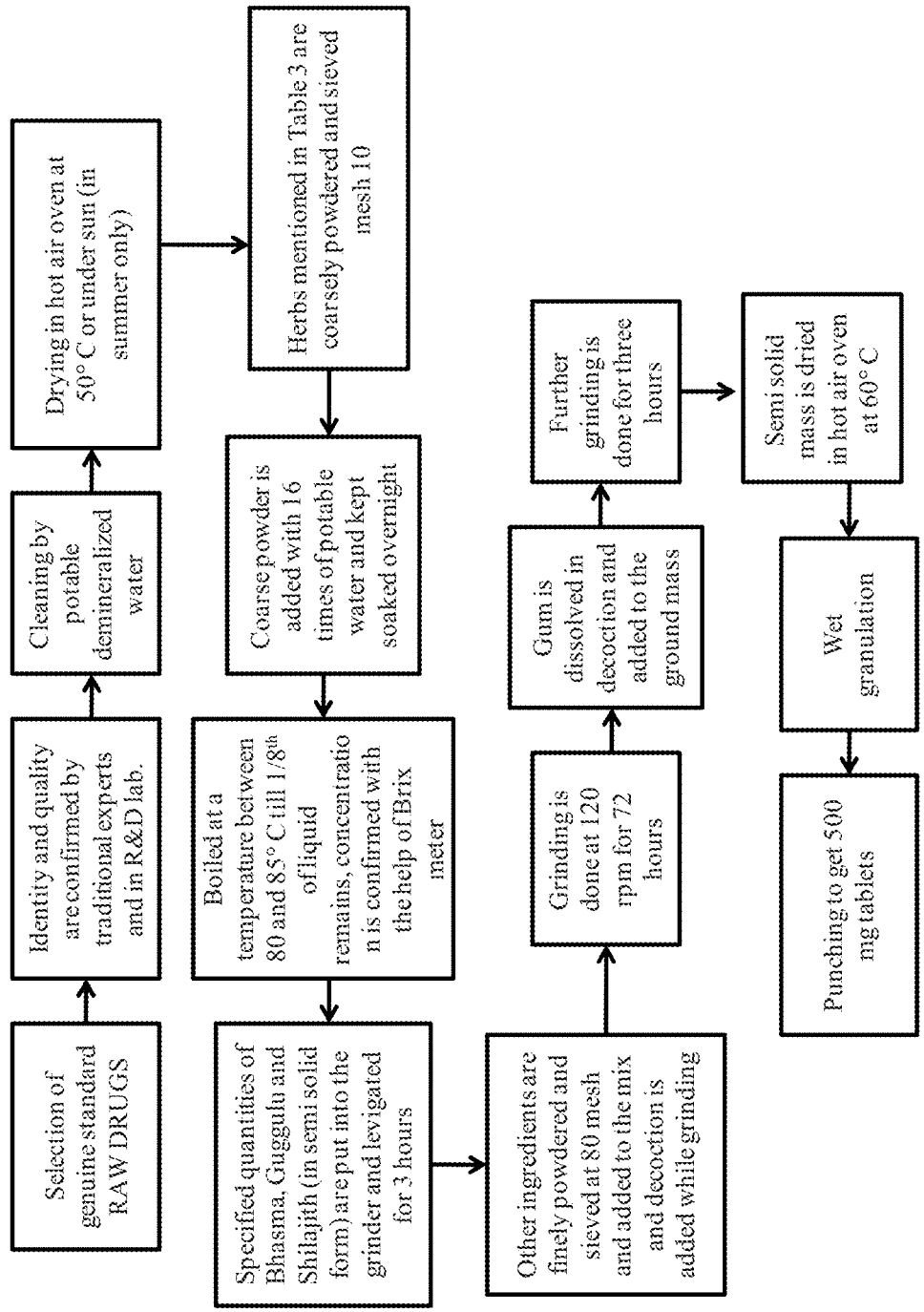
FIG. 2 depicts a flowchart for the preparation of fortified tablets.

Further, once the grinding decoction is added grinding is continued. In an embodiment, grinding is continued for about 72 hours, preferably at 120 rpm, to obtain a ground mass. In an embodiment, the method of preparation may further include adding excipient to the ground mass, wherein gum *acacia* may be added to the ground mass by dissolving in the grinding decoction while continuing grinding for 3 hours to obtain a semisolid mass. The method of preparation may further include drying at 50 degree Celsius, preferably in a hot air oven, wet granulating, punching to obtain 500 mg tablets. FIG. 2 depicts a flowchart for the preparation of fortified tablets. Table 3 depicts the Herb ingredients required for grinding (grinding herbs) in one of the preferred embodiments.

TABLE 3

List of Grinding herbs
Decoction of following herbs:

| 1 | Ishvaragola dry seeds | *Plantago ovate* | 1 part |
| 2 | Shalaparni dry plant | *Desmodium gangeticum* | 1 part |
| 3 | Prshniparni dry plant | *Uraria picta* | 1 part |
| 4 | Brhati dry root | *Solanum indicum* | 1 part |
| 5 | Kantakari dry plant | *Solanum xanthocarpum* | 1 part |
| 6 | Gokshura dry fruit | *Tribulus terrestris* | 1 part |
| 7 | Yavakshara alkali | *Hordeum vulgare* | 1 part |
| 8 | Kulattha dried seeds | *Dolichos biflorus* | 1 part |
| 9 | Hingu resin | Asafoetida | 1 part |
| 10 | Vrkshamla dried fruit rind | *Garcinia indica* | 1 part |
| 11 | Madhukapushpa | *Madhuca indica* | 1 part |
| 12 | Arjuna dry bark | *Terminalia arjuna* | 1 part |
| 13 | Shatavari fresh root | *Asparagus racemosus* | 1 part |
| 14 | Jeeraka dry fruit | *Cuminum cyminum* | 1 part |
| 15 | Chitraka dry root | *Plumbago rosea* | 1 part |
| 16 | Danti dry root | *Baliospermum montanum* | 1 part |
| 17 | Kumari fresh leaf | *Aloe vera* | 1 part |
| 18 | Devadaru dry heartwood | *Cedrus deodara* | 1 part |
| 19 | Khadira dry heartwood | *Acacia catechu* | 1 part |
| 20 | Kirata fresh whole plant | *Andrographis paniculata* | 1 part |
| 21 | Asana dry heartwood | *Pterocarpus marsupium* | 1 part |
| 22 | Vasa fresh leaves | *Adhatoda vasica* | 1 part |
| 23 | Krishna Jeeraka dried cremocarps | *Carum carvi* | 1 part |
| 24 | Karavellaka fresh fruit | *Momordica charantia* | 1 part |
| 25 | Methika dried seeds | *Trigonella foenum-graecum* | 1 part |
| 26 | Pugaphala dried nut | *Areca catechu* | 1 part |
|  | Jala | Water | 416 parts |
|  | Avashesha |  | ⅛ part of water |

The bhasmas that are used in the various embodiments of the disclosed herbal formulation may be prepared by methods that are generally known in the field. Bhasmas may be prepared by selecting genuine standard minerals as starting material such as Swarna makshika, Iron, alloy of tin, lead, pearl oysters, mica etc; drying in a hot air oven; purifying the mineral by triturating, quenching, boiling etc; triturating with herbal decoction; preparing into discs; drying of discs; preparing sharavasam puta, subjecting Sharavasam puta to Gaja puta, and powdering of discs once cooled. In an embodiment, the method is repeated 30 times till bhasma is obtained.

The starting materials used in the preparation of bhasmas may include standard minerals generally used in the field. In an embodiment, the preparation of Swarna makshika Bhasma includes Swarna makshika as the starting material. FIG. 1(*a*) depicts a flowchart for the preparation of Swarna makshika Bhasma using Swarna makshika as the starting material. In another embodiment, the preparation of Abhraka Bhasma includes Mica as the starting material. FIG. 1(*b*) depicts a flowchart for the preparation of Abhraka Bhasma using Mica as the starting material. In another embodiment, the preparation of Muktashukti Bhasma includes Pearl oyster as the starting material. FIG. 1(*c*) depicts a flowchart for the preparation of Muktashukti Bhasma using Pearl oyster as the starting material. In an embodiment, the preparation of Loha Bhasma includes steel iron as the starting material. FIG. 1(*d*) depicts a flowchart for the preparation of Loha Bhasma using steel iron as the starting material. In another embodiment, the preparation of Trivanga Bhasma includes alloy of tin and lead as the starting material. FIG. 1(*e*) depicts a flowchart for the preparation of Trivanga Bhasma using alloy of tin and lead as the starting material. Further, in an embodiment, the preparation of Pravala Bhasma includes Coral as the starting material. FIG. 1(*f*) depicts a flowchart for the preparation of Pravala Bhasma using Coral as the starting material.

The purification, or shodhana, of the mineral may be performed by generally known methods in the field. In an embodiment, the purification includes mixing the starting material with rock salt and lemon juice, and heating strongly till partially oxidized into reddish powder wherein it is further used in the preparation of Swarna makshika Bhasma. In another embodiment, the purification includes quenching the starting material in Cow's milk wherein it is further used in the preparation of Abhraka Bhasma. In an embodiment, the purification includes quenching the starting material in Kanjika (sour medicated gruel) wherein it is further used in the preparation of Mukta sukti Bhasma.

In another embodiment, the purification includes quenching the starting material in Triphala decoction wherein it is further used in the preparation of Loha Bhasma. In an embodiment, the purification includes melting and pouring the starting material in lime water wherein it is further used in the preparation of Trivanga Bhasma. In an embodiment, the purification includes boiling the starting material in alkaline solution of Barilla wherein it is further used in the preparation of Pravala Bhasma The herbal decoction/juices used for triturating may be any herbal decoction/juice that is generally used for triturating in the preparation of bhasmas. For example, the herbal decoction/juice may include triphala, lemon juice, Gomutra (cow's urine) etc. In an embodiment, the herbal decoction includes Nimbu Swarasa (Lemon juice) and Kulatha Kwatha (Decoction of *Dolichos biflorus*) wherein it is useful in the preparation of Swarna makshika bhasma.

In an embodiment, the herbal decoction includes *Aloe Vera* juice wherein it is useful in the preparation of Muktashukti Bhasma.

In an embodiment, the herbal decoction includes Arka Ksheera (Latex of *Calotropes procera*), Snuhi Ksheera (Latex of *Euphorbia neriifolia*), Vata Ksheera (Latex of *Ficus bengalensis*), Kakamachi Rasa (fresh juice of *Solanum nigrum* whole plant), Gokshura Kwatha (decoction of *Tribulus terrestris* fruits), Apamarga Rasa (Juice of *Achyranthus aspera* plant), Vata Praroha Swarasa (juice of aerial root of *Ficus bengalensis*), Gomutra (Cow urine), Tulasi Swarasa (Fresh juice of *Ocimum sanctum* leaves), Kadali Shipha Jala (Juice of plantain rhizome), Eranda patra rasa (Juice of *Ricinus communis* leaves), and Guda (Jaggery) wherein it is useful in the preparation of Abhraka Bhasma.

In an embodiment, the herbal decoction includes Triphala Kashaya (decoction of fruits of *Terminalia chebula, Terminalia bellerica* and *Emblica officinalis*) wherein it is useful in the preparation of Loha Bhasma.

In another embodiment, the herbal decoction includes fresh juice of leaves of *Aloe vera, Sesbania seban* and *Amaranthus spinosus* Linn.; fresh juice of roots of *Asparagus racemosus*; and Cow milk (Godugdha) wherein it is useful in the preparation of Pravala Bhasma.

In yet another embodiment, the herbal decoction includes dried roots of *Withania somnifera*, fresh roots of *Asparagus racemosus*, dried roots of *Glycerrhiza glabra* and water; and the herbal juice includes fresh juice of *Aloe vera* wherein it is useful in the preparation of Trivanga Bhasma Treatment Disclosed herein are embodiments of a method of treating/preventing/managing metabolic disorders. The metabolic disorders that may be treated include disorders caused by failure in metabolic processes, such as lipid metabolism disorders. The embodiments disclosed herein are instrumental in treating/preventing dyslipidemia and related disorders. Further, embodiments of a method of treating/managing Obesity are also disclosed herein.

In an embodiment, the method includes administering to a patient a composition as described in any of the embodiments disclosed herein. In an embodiment, the patient may include any individual in need of such treatment including ones having/suspected of having metabolic disorders or its symptoms. Further, the patient may also include any individual having/suspected of having dyslipidemia, obesity and related disorders. Dyslipidemia and related disorders in the various embodiments herein may include conditions such as hyperlipidemia, hypolipidemia, hypercholesterolemia, hypertriglyceridemia, cardio vascular diseases, cerebro vascular diseases, stroke, pancreatitis, steatohepatitis, atherosclerosis, obesity, hyperglycemia, metabolic syndrome, etc. The patient may also include any individual having any complication associated abnormal lipid levels.

In a preferred embodiment, the method includes administering to a patient a composition having herb element, mineral element and suitable excipient, wherein the herb element includes *Premna integrifolia* (2 to 6 wt %), *Plumbago rosea* (2 to 6 wt %), *Commiphora mukul* (2 to 6 wt %), *Emblica officinalis* (1 to 4 wt %), *Terminalia bellerica* (1 to 4 wt %), *Terminalia chubula* (1 to 4 wt %), *Zingiber officinalis* (1 to 4 wt %), *Piper longum* (1 to 4 wt %), *Piper nigrum* (1 to 4 wt %), *Embelia ribes* (1 to 4 wt %), *Curcuma longa* (1 to 4 wt %), *Terminalia arjuna* (1 to 4 wt %), *Sida rhombifolia* (1 to 4 wt %), *Withania somnifera* (1 to 4 wt %), *Inula racemose* (1 to 4 wt %), *Punica grnatum* (1 to 4 wt %), *Nardostachys jatamansi* (1 to 4 wt %), *Boerhavia diffusa* (1 to 4 wt %), *Picrorhiza kurroa* (1 to 4 wt %), *Ocimum sanctum* (1 to 4 wt %), *Azadirachta indica* (1 to 4 wt %), *Aristolochia indica* (1 to 4 wt %), *Aegle marmelos* (1 to 4 wt %), *Cyperus rotundas* (1 to 4 wt %), *Hemidesmus indicus* (1 to 4 wt %), *Trichosanthus dioica* (1 to 4 wt %), *Sanatalum album* (1 to 4 wt %), *Glycerrhiza glabra* (1 to 4 wt %), *Woodfordia fruiticosa* (1 to 4 wt %), *Mucuna pruriens* (1 to 4 wt %), *Myrica nagi* (1 to 4 wt %), *Syzygium cumini* (1 to 4 wt %), *Tinospora cordifolia* (1 to 4 wt %), *Bamboo manna* (1 to 4 wt %); and mineral element includes Shilajit (2 to 6 wt %) and at least one of bhasma selected from Abhraka bhasma (1 to 4 wt %), Swarnamakshika bhasma (1 to 4 wt %), Pravala bhasma (1 to 4 wt %), Muktashukti Bhasma (1 to 4 wt %), Loha bhasma (1 to 4 wt %) and Trivanga bhasma (1 to 4 wt %).

In an embodiment, the disclosed formulation may be used such that it acts as at least one of anti-lipid, free radical scavenging and hypolipidemic agent.

The disclosed method of treatment may be used as a primary line of treatment or as an adjunct to other treatment methods for metabolic disorders.

The patient may be administered a therapeutically effective amount of the embodiments of the disclosed formulation. The therapeutically effective amount may vary depending on the patient. In an embodiment, the therapeutically effective amount is 500 to 1000 mg administered one to three times a day.

Figure 3:
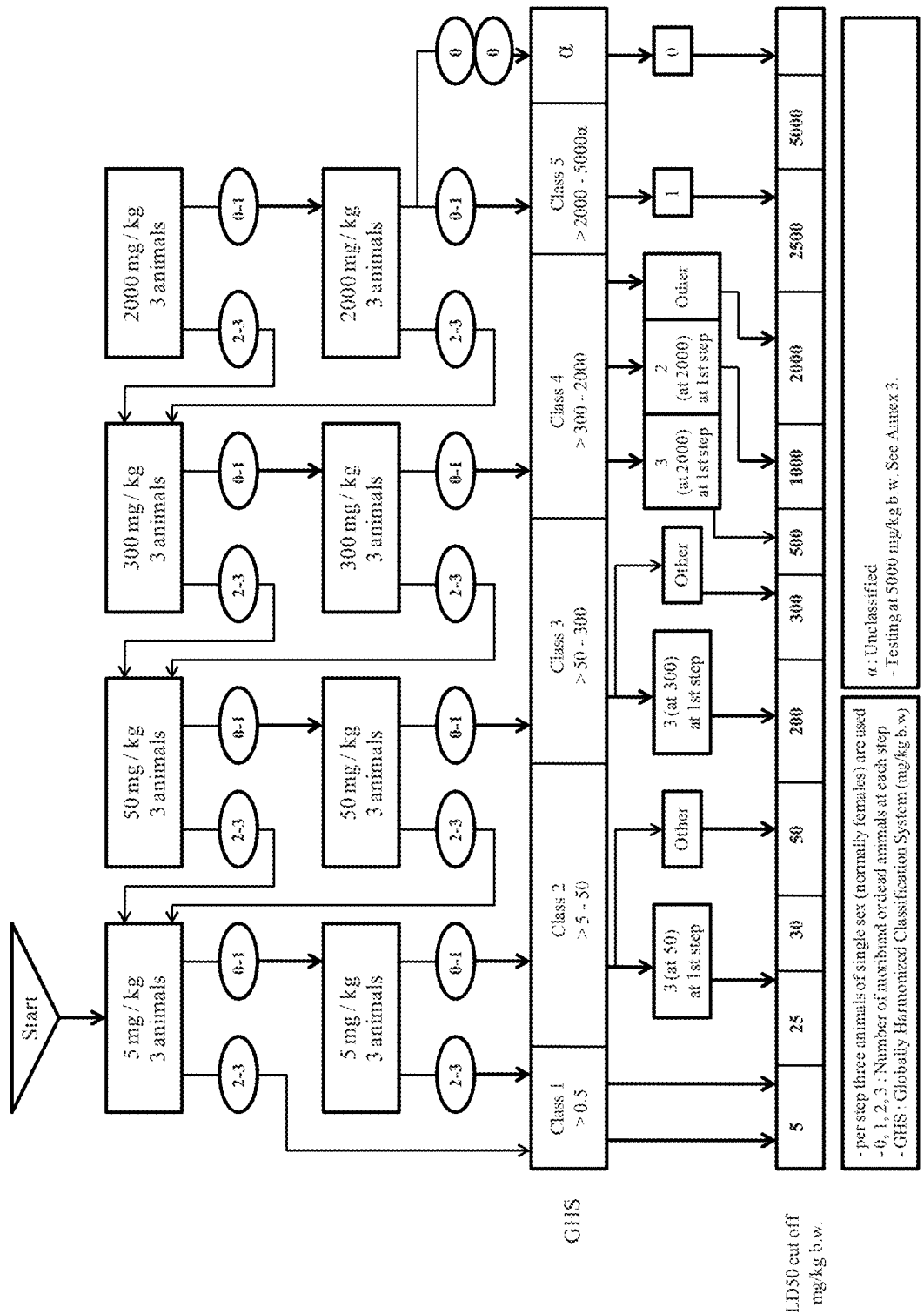
FIG. 3 is schematic representation of the Acute oral toxic class method.

Embodiments of the disclosed formulation were subjected to acute oral toxicity study according to OECD guidelines 423 (Acute toxic class method). FIG. 3 provides a schematic representation of the acute toxic class method. The toxicity study is hereunder described by way of an example. Embodiments are further described herein by reference to the following examples by way of illustration only, and should not be construed to limit the scope of the claims provided herewith. It will be apparent to those skilled in the art that many modifications, both to materials and methods, may be practiced without departing from the scope of the claims.

Example 1: Acute Oral Toxicity Study

The acute toxic class method, as depicted in FIG. 3, is a stepwise procedure with 3 animals of a single sex per step. Depending on the mortality and/or moribund status of the animals, on the average 2-4 steps is necessary to allow judgment on the acute toxicity of the test drug. The method used defined doses (5, 50, 500, 2000 mg/kg body weight). The results of this study allow a drug to be ranked and classified according to the Globally Harmonized System (GHS) for the classification of chemical, which cause acute toxicity.

Selection of Animal Species

The preferred rodent species is rat, although other rodent species may be used. Generally females are used.

Housing and Feeding Conditions

The temperature in the experimental animal room should be 22° C. (+3° C.). Lighting should be artificial, the sequence being 12 hours light, 12 hours dark. For feeding, conventional laboratory diets are used with an unlimited supply of drinking water.

Preparation of Animals

The animals are randomly selected, marked to permit individual identification, and kept in their cages for at least 5 days prior to dosing to allow for acclimatisation to the laboratory conditions.

Preparation of Test Drug Solution:

Test drug was suspended in 10% aqueous Tween 80 and used orally for toxicological and Pharmacological evaluations.

Procedure

As most of the herbs are safe at the dose level of 2000 mg/kg according to the guidelines 2000 mg/kg is used as starting dose. Test drug is administered in a single dose.

ment. LD50 cut off mg/kg body weight was observed as X (unclassified) and Globally Harmonized System (GHS) classes also comes under X (Unclassified). Table 4 depicts the Behavioral profile.

TABLE 4

Behavioral profile of acute toxicity data

| | | Before drug administration | | | After drug administration | | |
|---|---|---|---|---|---|---|---|
| No | Parameters | Rat1 | Rat2 | Rat3 | Rat1 | Rat2 | Rat3 |
| 1 | Body weight | 150 gm | 150 gm | 150 gm | 165 gm | 160 gm | 165 gm |
| 2 | Alertness | + | + | + | + | + | + |
| 3 | Passivity | + | + | + | + | + | + |
| 4 | Grooming | − | − | − | − | − | − |
| 5 | Restlessness | − | − | − | − | − | − |
| 6 | Aggressiveness | − | − | − | − | − | − |
| 7 | Touch response | + | + | + | + | + | + |
| 8 | Righting reflex | + | + | + | + | + | + |
| 9 | Tremors | − | − | − | very mild | very mild | very mild |
| 10 | Convulsion | − | − | − | − | − | − |
| 11 | Gripping strength | + | + | + | + | + | + |
| 12 | Pinna reflex | + | + | + | + | + | + |
| 13 | Corneal reflex | + | + | + | + | + | + |
| 14 | Writhing reflex | − | − | − | − | − | − |
| 15 | Urination | N | N | N | N | N | N |
| 16 | Salivation | N | N | N | N | N | N |
| 17 | Skin color | N | N | N | N | N | N |
| 18 | Lacrimation | N | N | N | N | N | N |
| 19 | Locomotion | N | N | N | R | R | R |
| 20 | Catalepsy | − | − | − | − | − | − |
| 21 | Eyelid closure | N | N | N | N | N | N |
| 22 | Scratching | − | − | − | − | − | − |

'N'—Normal,
'R'—Reduced,
'+'—Present,
'−'—Absent

Animals are fasted prior to experimentation. Following the period of fasting, the animals are weighed and the test substance administered. After the substance has been administered, food was withheld for a further 3-4 hours.

Number of Animals and Dose Levels

Three animals are used for each step. And the same dose is repeated in another 3 animals.

Observations

Animals are observed individually after dosing for the first 30 minutes, periodically during the first 24 hours, with special attention given during the first 4 hours, and daily thereafter, for a total of 14 days. All observations are systematically recorded. Observations include Changes in skin and fur, eyes and mucous membranes, Somatomotor activity and behaviour pattern, Tremors, convulsions, salivation, diarrhoea, lethargy, sleep and coma.

Body Weight

Individual weights of animals are determined shortly before the test substance is administered and weekly thereafter. Weight changes are calculated and recorded. At the end of the test, surviving animals are weighed.

Results

A starting dose of 2000 mg/kg body weight/p.o of Test drug was administered to 3 male rats, observed for three days. There was no considerable change in body weight before and after treatment of the experiment and no signs of toxicity were observed. When the experiments were repeated again with the same dose level, and observed for 14 days no changes were observed from the first set of experi- Embodiments of the Disclosed formulation (also referred as Test product or Test drug) were further evaluated for efficacy of hypolipidemic activity, as described hereunder by way of examples. Embodiments are further described herein by reference to the following examples by way of illustration only, and should not be construed to limit the scope of the claims provided herewith. It will be apparent to those skilled in the art that many modifications, both to materials and methods, may be practiced without departing from the scope of the claims.

Example 2: Assessment of Hypolipidemic Activity

Animals Used:

Male Wistar (body weight 150-200 g) rats were used for the study. They were allowed ad libitum access to water and food. All the animals were subjected to estimation of lipid profile. Animals showed normal lipid profile were selected for further study. Rats were divided into three groups of six rats each.

Treatment:
 Group I: Control Diet
 Group II: Hypercholestremic diet
 Group III: Hypercholestremic diet+Test drug
Hypercholestremia was induced by supplementing Atherogenic diet comprising 40% groundnut powder, 20% cholesterol, 40% normal rat food.
 Procedure:
Hypercholestremic diet was administered for 45 days. Then lipid profile was carried out for all the animals in order to confirm elevated cholesterol level. All hypercholestermic rats were then subjected to the drug treatment for next 15 days. On 16$^{th}$ day blood sample was withdrawn from the retro-orbital plexus of overnight fasted rats. Serum was separated and Total cholesterol, HDL, LDL and Triglycerides were estimated using commercially available kits. Finally, the animals were dissected and the aorta is removed and kept in formol-saline for histopathological examination.

Figure 4:
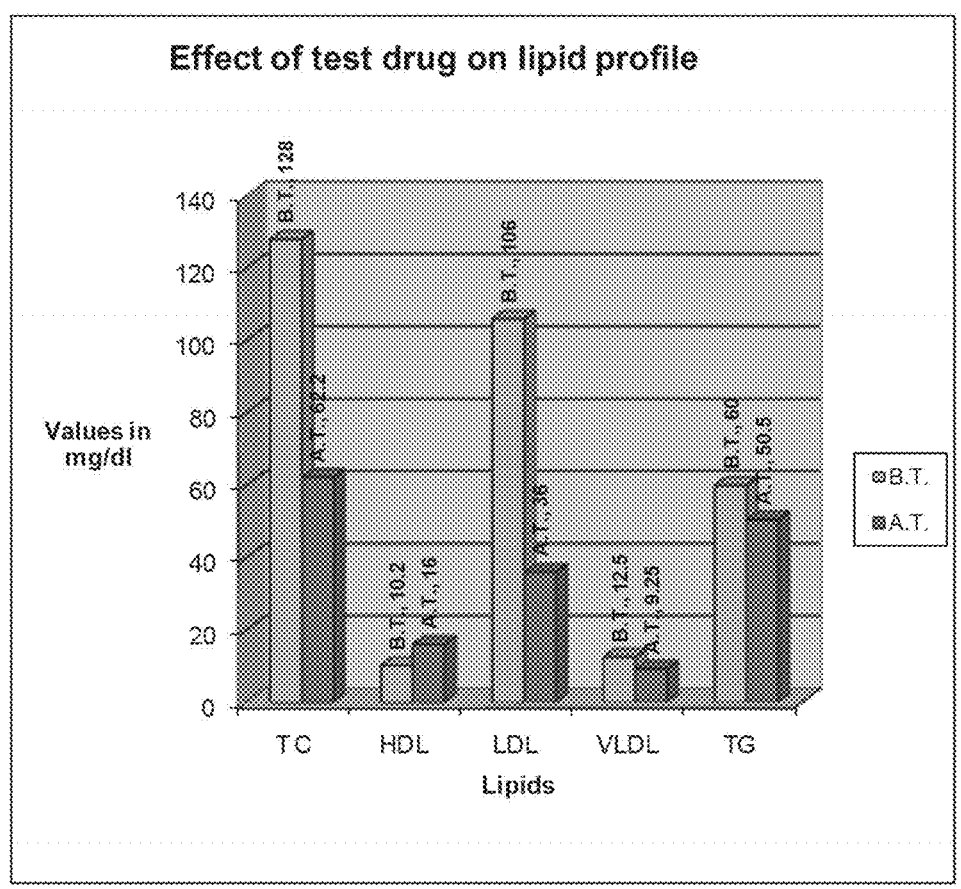
FIG. 4 depicts the effect of the disclosed formulation on lipid profile.

Results:

The studies carried out proved that highly significant reduction of Total Cholesterol, Low Density Lipoprotein (LDL), triglycerdes, atherogenic index and increase in High Density Lipoprotein (HDL) indicate promising results of Test drug as hypocholestremic (cholesterol lowering) drug. Table 5 depicts the lipid profile that was observed before and after treatment with test drug. FIG. 4 is a graph depicting the effect of the test drug on lipid profile.

TABLE 5

Lipid profile observed before and after treatment with test drug. Statistical significance test was done by paired 't' test.

| Lipid profile | Before Atherogenic diet (Normal) | After atherogenic diet (Hyper cholestremic) | After test drug treatment |
|---|---|---|---|
| TC | 51.40 ± 6.24 | 128 ± 12.32a** | 62.20 ± 9.74b** |
| HDL | 19.40 ± 3.63 | 10.2 ± 2.04a* | 16 ± 1.88b* |
| LDL | 23.1 ± 4.18 | 106 ± 19.06a** | 36 ± 7.38b** |
| VLDL | 8.05 ± 0.98 | 12.5 ± 2.06a* | 9.25 ± 0.86b* |
| TG | 45 ± 9.86 | 60 ± 14.02a* | 50.5 ± 11.52b* |

Figure 5A:
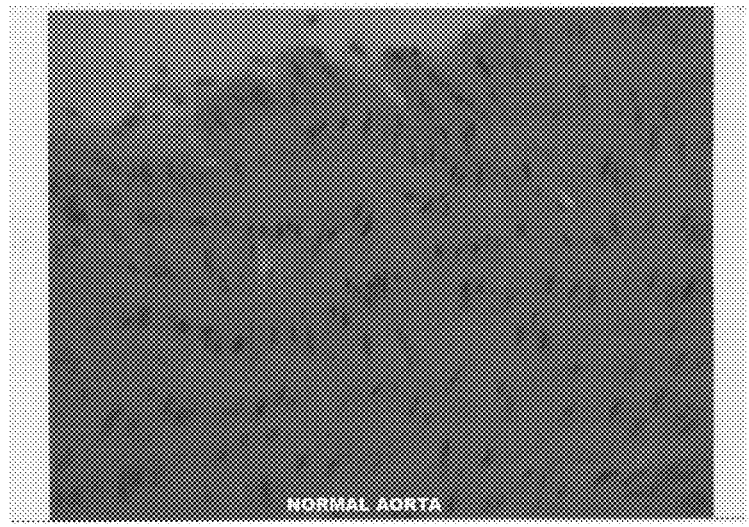
FIG. 5(a) is a photomicrograph of normal aorta observed in Histopathological studies.
Figure 5B:
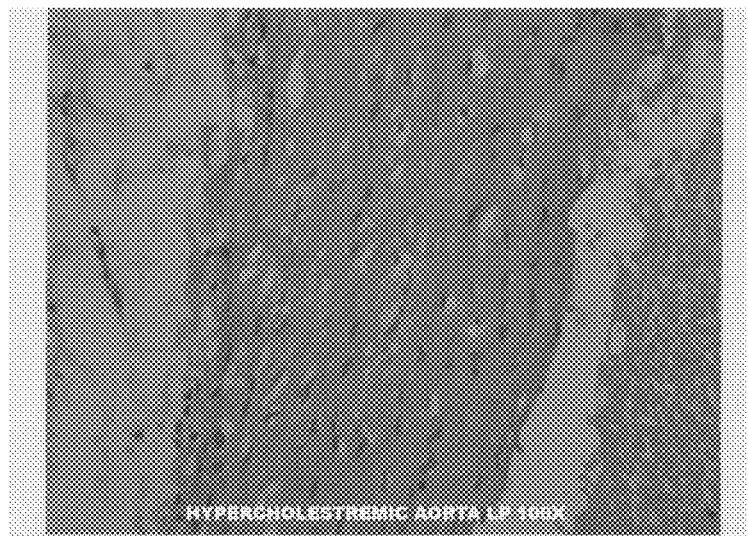
FIG. 5(b) is a photomicrograph of hypercholestremic aorta (LP 100×) observed in Histopathological studies.
Figure 5C:
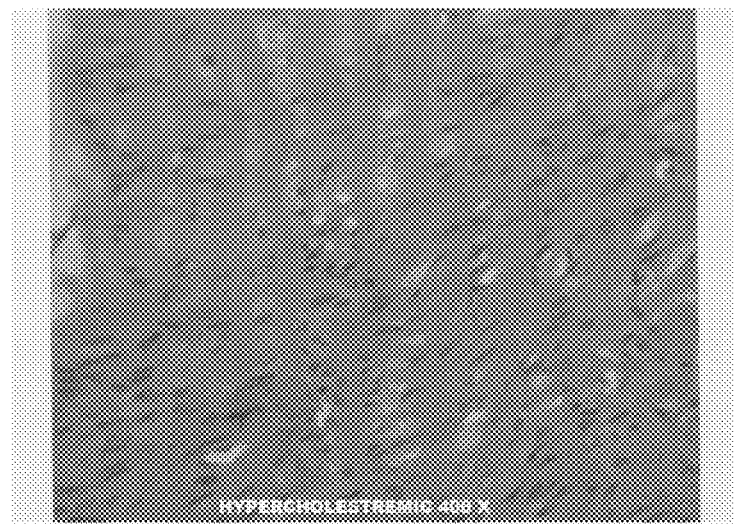
FIG. 5(c) is a photomicrograph of hypercholestremic aorta (400×) observed in Histopathological studies.
Figure 5D:
FIG. 5(d) is a photomicrograph of test drug treated aorta observed in Histopathological studies, according to embodiments as disclosed herein.

Results are expressed as Mean ± S.E.M of 6 number of animals.
a—comparison made between Normal and hypercholestremic rats
b—comaparison made between Hypercholestremic and test drug treated rats.
*$p < 0.01$,
**$p < 0.001$ Histopathological studies of Test drug treated rats have proved that Test drug has excellent tissue protective activities against fatty infiltration and tissue damage. FIGS. 5(a), 5(b), 5(c) and 5(d) represent photomicrographs of the histopathological studies. FIG. 5(a) depicts photomicrograph of normal aorta, FIG. 5(b) depicts photomicrograph of Hypercholestremic aorta 100×, FIG. 5(c) depicts photomicrograph of hypercholestremic aorta 400× and FIG. 5(d) depicts photomicrograph of Test drug treated aorta.

Example 3: Clinical Study to Assess the Efficacy of the Test Drug

Aim:

To assess the efficacy of the test drug on lipid profile of hyperlipidemic patients with or without obesity.

Materials and Method:

300 patients were evaluated for general health and lipid profile through a medical history and a thorough physical examination.

Inclusion Criteria:
1. Patients of either sex aged 18-70 years.
2. Patients having LDLc 100 mg/dl-160 mg/dl and/or Total cholesterol 200 mg/dl and above and Triglycerides 200 mg/dl and above Exclusion Criteria:
1. Patients who have received any cholesterol lowering medication (Modern Drug) within last 8 weeks.
2. Patients having Type III and Type IV hypercholesterolaemia.

After screening, 250 patients qualified for the study, their ages ranged from 18 to 70 years, with a median of 46. There were 147 male and 103 female patients. Each patient underwent routine hematological and biochemical laboratory investigations. Patients were asked not to eat any food, except for water, for 12 to 14 hours before taking blood samples. Routine urine analysis and electrocardiography were also carried out. The study planned was single arm open labeled clinical study with pre and post-test design carried out for 8 weeks. The written and informed consent was obtained from all the patients.

Dose and duration: 2 tablets (500 mg×02) twice daily after food swallowed with water, given for 8 weeks.

Assessment was done after four and eight weeks. A registered dietician interviewed the patients and instructed them to have diet with low cholesterol and saturated fats.

The clinical side effects if any were recorded at each visit and discussed with the patient to know the nature, severity and frequency. Patients were seen by the same dietician at every clinic visit throughout the study and were instructed to follow the same diets and to maintain weight, physical activity levels and smoking frequency for the duration of the study. The results were analysed using paired 't' test.

Results:

Of the 250 patients who entered the active-treatment phase of the study, 6 were excluded because of non-compliance and 244 patients completed the study. The patients followed fairly uniform dietary patterns during the trial and their compliance was assured by routine interviews with the dietician and review of the computer's analysis of dietary records at every clinic visit. Routine follow-up by the dietician resulted in good overall dietary compliance and accounted for the attainment, in many patients of normal cholesterol levels in both the drug treatment. Results of those patients taking test drug showed a reduction of total cholesterol from 254.30±7.33 mg/dl to 192.28±9.24 mg/dl after four weeks and 190.01±9.11 mg/dl after eight weeks of treatment. Reduction in triglycerides from 226.00±22.37 to 166.70±18.32 mg/dl in four weeks which further reduced to 164.35±16.32 mg/dl after eight weeks. Similarly, LDL levels were reduced from 170.01±7.21 to 115.1±7.90 mg/dl at the end of four weeks which further got reduced to 112.10±7.90 mg/dl after eight weeks. VLDL levels were reduced from 42.56±4.14 to 38.52±4.06 mg/dl at the end of four weeks which further got reduced to 37.41±4.98 mg/dl after eight weeks. Triglycerides levels were also reduced from 216.0±26.37 mg/dl. HDL level got marginally increased from 38.23±2.87 mg/dl to 40.11±2.82 in four weeks which further got improved up to 41.10±4.02 mg/dl after eight weeks of therapy. Table 6 depicts the effect of the test drug on lipid levels (Total cholesterol, Triglycerides, LDL, HDL and VLDL).

TABLE 6

Effect of test drug on level of lipids

| Parameters | Before treatment | After 4 weeks of treatment | After 8 weeks of treatment |
|---|---|---|---|
| Total cholesterol (mg/dl) | 254.30 ± 7.33 | 192.28 ± 9.24* | 190.01 ± 9.11* |
| Triglycerides (mg/dl) | 226.00 ± 22.37 | 166.70 ± 18.32* | 164.35 ± 16.2* |
| HDL (mg/dl) | 38.23 ± 2.87 | 40.11 ± 2.82 | 41.10 ± 4.02* |
| LDL (mg/dl) | 170.01 ± 7.21 | 115.14 ± 8.44* | 112.10 ± 7.90* |
| VLDL (mg/dl) | 42.56 ± 4.14 | 38.52 ± 4.06* | 37.41 ± 4.98* |

*$p < 0.001$ as compared to the before treatment value

Observations: According to the results of the study, test drug has significantly reduced the level of total cholesterol, LDL, VLDL and triglycerides. Marginal increase in HDL level is also noticed.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. A herbal formulation for treatment and management of Metabolic disorders and associated complications, said formulation comprising a therapeutically effective amount of the following herb element and of the following mineral element:
   (i) a herb element comprising *Premna integrifolia*, *Plumbago rosea* and *Commiphora mukul* (Guggulu), or extracts thereof; and
   (ii) a mineral element comprising of shilajit and bhasma.

2. The herbal formulation as claimed in claim 1, wherein said herb element further comprises at least one herb selected from the group consisting of *Emblica officinalis, Terminalia bellerica, Terminalia chebula, Zingiber officinalis, Piper longum, Piper nigrum, Embelia ribes, Curcuma longa, Terminalia arjuna, Sida rhombifolia, Withania somnifera, Inula racemosa, Punica granatum, Nardostachys jatamansi, Boerhavia diffusa, Picrorhiza kurroa, Ocimum sanctum, Azadirachta indica, Aristolochia indica, Aegle marmelos, Cyperus rotundas, Hemidesmus indicus, Trichosanthes dioica, Santalum album, Glycrrhiza glabra, Woodfordia fruticosa, Mucuna pruriens, Myrica nagi, Syzygium cumini, Tinospora cordifolia* and *Bamboo manna*, or extracts thereof.

3. The herbal formulation as claimed in claim 1, wherein said mineral element comprises at least one bhasma selected from a group consisting of Abhraka bhasma, Swarna Makshika bhasma, Pravala bhasma, Mukta shukti bhasma, Loha bhasma, and Trivanga bhasma.

4. The herbal formulation as claimed in claim 3, wherein said Abhraka bhasma is present in an amount ranging from 1 to 4 wt %, Swarna makshika bhasma is present in an amount ranging from 1 to 4 wt %, Pravala bhasma is present in an amount ranging from 1 to 4 wt %, Muktashukti bhasma is present in an amount ranging from 1 to 4 wt %, Loha bhasma is present in an amount ranging from 1 to 4 wt %, and/or Trivanga bhasma is present in an amount ranging from 1 to 4 wt %.

5. The herbal formulation as claimed in claim 1, wherein said *Premna integrifolia* is present in an amount ranging from 2 to 6 wt %, *Plumbago rosea* is present in an amount ranging from 2 to 6 wt % and *Commiphora mukul* is present in an amount ranging from 2 to 6 wt %.

6. The herbal formulation as claimed in claim 1, wherein shilajit is present in an amount ranging from 2 to 6 wt %.

7. The herbal formulation as claimed in claim 2, wherein said *Emblica officinalis* is present in an amount ranging from 1 to 4 wt %, *Terminalia bellerica* is present in an amount ranging from 1 to 4 wt %, *Terminalia chebula* is present in an amount ranging from 1 to 4 wt %, *Zingiber officinalis* is present in an amount ranging from 1 to 4 wt %, *Piper longum* is present in an amount ranging from 1 to 4 wt %, *Piper nigrum* is present in an amount ranging from 1 to 4 wt %, *Embelia ribes* is present in an amount ranging from 1 to 4 wt %, *Curcuma longa* is present in an amount ranging from 1 to 4 wt %, *Terminalia arjuna* is present in an amount ranging from 1 to 4 wt %, *Sida rhombifolia* is present in an amount ranging from 1 to 4 wt %, *Withania somnifera* is present in an amount ranging from 1 to 4 wt %, *Inula racemosa* is present in an amount ranging from 1 to 4 wt %, *Punica granatum* is present in an amount ranging from 1 to 4 wt %, *Nardostachys jatamansi* is present in an amount ranging from 1 to 4 wt %, *Boerhavia diffusa* is present in an amount ranging from 1 to 4 wt %, *Picrorhiza kurroa* is present in an amount ranging from 1 to 4 wt %, *Ocimum sanctum* is present in an amount ranging from 1 to 4 wt %, *Azadirachta indica* is present in an amount ranging from 1 to 4 wt %, *Aristolochia indica* is present in an amount ranging from 1 to 4 wt %, *Aegle marmelos* is present in an amount ranging from 1 to 4 wt %, *Cyperus rotundas* is present in an amount ranging from 1 to 4 wt %, *Hemidesmus indicus* is present in an amount ranging from 1 to 4 wt %, *Trichosanthes dioica* is present in an amount ranging from 1 to 4 wt %, *Santalum album* is present in an amount ranging from 1 to 4 wt %, *Glycyrrhiza glabra* is present in an amount ranging from 1 to 4 wt %, *Woodfordia fruticosa* is present in an amount ranging from 1 to 4 wt %, *Mucuna pruriens* is present in an amount ranging from 1 to 4 wt %, *Myrica nagi* is present in an amount ranging from 1 to 4 wt %, *Syzygium cumini* is present in an amount ranging from 1 to 4 wt %, *Tinospora cordifolia* is present in an amount ranging from 1 to 4 wt % and *Bamboo manna* is present in an amount ranging from 1 to 4 wt %.

8. The herbal formulation as claimed in claim 1, further comprising a suitable excipient, preferably gum *acacia*.

9. The herbal formulation as claimed in claim 1, further comprising one or more additives selected from the group consisting of a flavor, a colorant, a preservative, and a pH adjuster.

10. The herbal formulation as claimed in claim 1, wherein said formulation is administered in a form selected from a group consisting of powder, emulsion, tablets, capsules, troches and pills.

11. The herbal formulation as claimed in claim 1, wherein said formulation is in the form of a tablet.

12. The herbal formulation as claimed in claim 11, wherein said tablet is in the form of 500 mg tablets.

13. A process for the preparation of the herbal formulation as claimed in claim 1, comprising:
   (a) Levigating the bhasma, *Commiphora mukul* (Guggulu) and shilajit;
   (b) adding a decoction of herbs to the mixture made in step (a); and
   (c) grinding the mixture of step (b) to obtain a ground mass, wherein the herbs comprise *Premna integrifolia* and *Plumbago rosea*.

14. The process for the preparation of herbal formulation as claimed in claim 13, wherein said bhasma is selected from a group consisting of Abhraka bhasma, Swarna makshika bhasma, Pravala bhasma, Muktashukti Bhasma, Loha bhasma, and Trivanga bhasma.

15. The process for the preparation of herbal formulation as claimed in claim 13, wherein said herbs further comprise a finely powdered form of at least one herb selected from the group consisting of dried roots of *Premna integrifolia*,

*Plumbago rosea, Sida rhombifolia, Withania somnifera, Inula racemosa, Boerhavia diffusa, Picrorhiza kurroa, Aristolochia indica, Aegle marmelos, Cyperus rotundas, Hemidesmus indicus* and *Glycrrhiza glabra*; dried fruits of *Emblica officinalis, Terminalia bellerica, Terminalia chebula, Piper longum, Piper nigrum* and *Embelia ribes*: dried rhizome of *Zingiber officinalis, Curcuma longa* and *Nardostachys jatamansi*; dried stem bark of *Terminalia arjuna, Azadirachta indica, Myrica nagi* and *Syzygium cumini*; dried exocarp and epicarp of *Punica granatum*; dried leaves of *Ocimum sanctum*; dried whole plant of *Trichosanthes dioica*; dried heartwood of *Santalum album*; dried flowers of *Woodfordia fruticosa*; dried seeds of *Mucuna pruriens*; and starchy extract of stem of *Tinospora cordifolia*.

16. The process for the preparation of herbal formulation claimed in claim 13, wherein said grinding decoction is a decoction of at least one herb selected from the group consisting of powdered dry seeds of *Plantago ovata*, powdered dry plant of *Desmodium gangeticum*, powdered dry plant of *Uraria picta*, powdered dry roots of *Solanum indicum*, powdered dry plant of *Solanum xanthocarpum*, powdered dry fruits of *Tribulus terrestris*, Yavakshara alkali of *Hordeum vulgare*, powdered dry seeds of *Dolichos biflorus*, resin of *Asafoetida*, powdered dry fruit rind of *Garcinia indica*, powdered dry flower of *Madhuca indica*, powdered dry bark of *Terminalia arjuna*, fresh root of *Asparagus racemosus*, powdered dry fruit of *Cuminum cyminum*, powdered dry root of *Plumbago rosea*, powdered dry root of *Baliospermum montanum*, fresh leaf of *Aloe vera*, powdered dry heartwood of *Cedrus deodara*, powdered dry heartwood of *Acacia catechu*, fresh whole plant of *Andrographis paniculata*, powdered dry heartwood of *Pterocarpus marsupium*, fresh leaves of *Adhatoda vasica*, powdered dry cremocarps of *Carum carvi*, fresh fruit of *Momordica charantia*, powdered dry seeds of *Trigonella foenum-graecum* and powdered dry nut of *Areca catechu*.

17. A method of treatment for metabolic disorders and associated complications, comprising administering a therapeutically effective amount of the formulation claimed in claim 1.

18. A method of treatment for dyslipidemia and related disorders, comprising administering a therapeutically effective amount of the formulation claimed in claim 1.

19. A method of treatment for obesity and related disorders, comprising administering a therapeutically effective amount of the formulation claimed in claim 1.

20. The method of treatment for metabolic disorders and associated complications as claimed in claim 17, wherein said therapeutically effective amount is 500 to 1000 mg administered one to three times a day.

21. The method of treatment for metabolic disorders and associated complications as claimed in claim 17, wherein said formulation is administered along with administration of at least one other medication prescribed for treatment of metabolic disorder and associated complications.

\* \* \* \* \*